US007279337B2

(12) United States Patent
Zhu

(10) Patent No.: US 7,279,337 B2
(45) Date of Patent: Oct. 9, 2007

(54) METHOD AND APPARATUS FOR SEQUENCING POLYMERS THROUGH TUNNELING CONDUCTANCE VARIATION DETECTION

(75) Inventor: Miao Zhu, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 208 days.

(21) Appl. No.: 10/797,651

(22) Filed: Mar. 10, 2004

(65) Prior Publication Data
US 2005/0202444 A1    Sep. 15, 2005

(51) Int. Cl.
*G01N 35/00*    (2006.01)
*G01N 33/48*    (2006.01)
*G01N 33/00*    (2006.01)
*G01N 15/06*    (2006.01)
*C12Q 1/68*    (2006.01)

(52) U.S. Cl. .................. 436/43; 422/50; 422/68.1; 422/82.01; 436/63; 436/86; 436/89; 436/149; 73/1.01; 73/1.02

(58) Field of Classification Search .................. 422/50, 422/68.1, 82.01; 73/1.01, 1.02; 436/43, 436/63, 86, 89, 149
See application file for complete search history.

(56) References Cited

U.S. PATENT DOCUMENTS

| 3,566,262 | A |  | 2/1971 | Thompson |
| 5,795,782 | A |  | 8/1998 | Church et al. |
| 5,843,767 | A |  | 12/1998 | Beattie |
| 6,015,714 | A |  | 1/2000 | Baldarelli et al. |
| 6,267,872 | B1 |  | 7/2001 | Akeson et al. |
| 6,355,420 | B1 |  | 3/2002 | Chan |
| 6,362,002 | B1 |  | 3/2002 | Denison et al. |
| 6,627,067 | B1 |  | 9/2003 | Branton et al. |
| 6,905,586 | B2 | * | 6/2005 | Lee et al. ............... 204/600 |
| 2002/0119455 | A1 |  | 8/2002 | Chan |
| 2002/0197618 | A1 |  | 12/2002 | Sampson |
| 2003/0044816 | A1 |  | 3/2003 | Denison et al. |
| 2003/0141189 | A1 |  | 7/2003 | Lee et al. |
| 2003/0211502 | A1 | * | 11/2003 | Sauer et al. ............... 435/6 |
| 2004/0124084 | A1 | * | 7/2004 | Lee et al. ............... 204/600 |
| 2004/0144658 | A1 | * | 7/2004 | Flory ............... 205/777.5 |

FOREIGN PATENT DOCUMENTS

| EP | 1 441 213 A1 | 7/2004 |
| EP | 1 443 318 A1 | 8/2004 |
| WO | WO 01/81896 A1 | 11/2001 |
| WO | WO 02/42757 A1 | 5/2002 |

OTHER PUBLICATIONS

European Search Report Dated: Dec. 3, 2004.
Kasianowicz, J.J. et al. (Nov. 1996) "Characterization of individual polynucleotide molecules using a membrane channel." PNAS 93, 13770-13773.

(Continued)

*Primary Examiner*—Brian Sines

(57) ABSTRACT

Systems and methods of identifying molecules of polymers such as, for example, a nucleic acid, are described. The method involves centering a bias voltage across a pair of nanoelectrodes separated by a channel that corresponds to one of any of the energy differences between any two internal energy levels of a molecule of interest, and modulating the bias voltage with a modulation waveform while the molecule of interest is in the channel. An electrical signal characteristic of the molecule of interest is derived from the tunneling current between the nanoelectrodes, and the characteristic electrical signal is compared with known values of the signal for chemically-known molecules in order to identify the molecule of interest. Multiple pairs of nanoelectrodes may be employed to identify more reliably a single molecule or multiple molecules.

31 Claims, 3 Drawing Sheets

OTHER PUBLICATIONS

Stipe, B.C. et al. (Jun. 1998) "Single-Molecule Vibrational Spectroscopy and Microscopy." Science 280, 1732-1735.

Meller, A. et al. (Feb. 2000). "Rapid nanopore discrimination between single polynucleotide molecules." PNAS 97(3), 1079-1084.

* cited by examiner

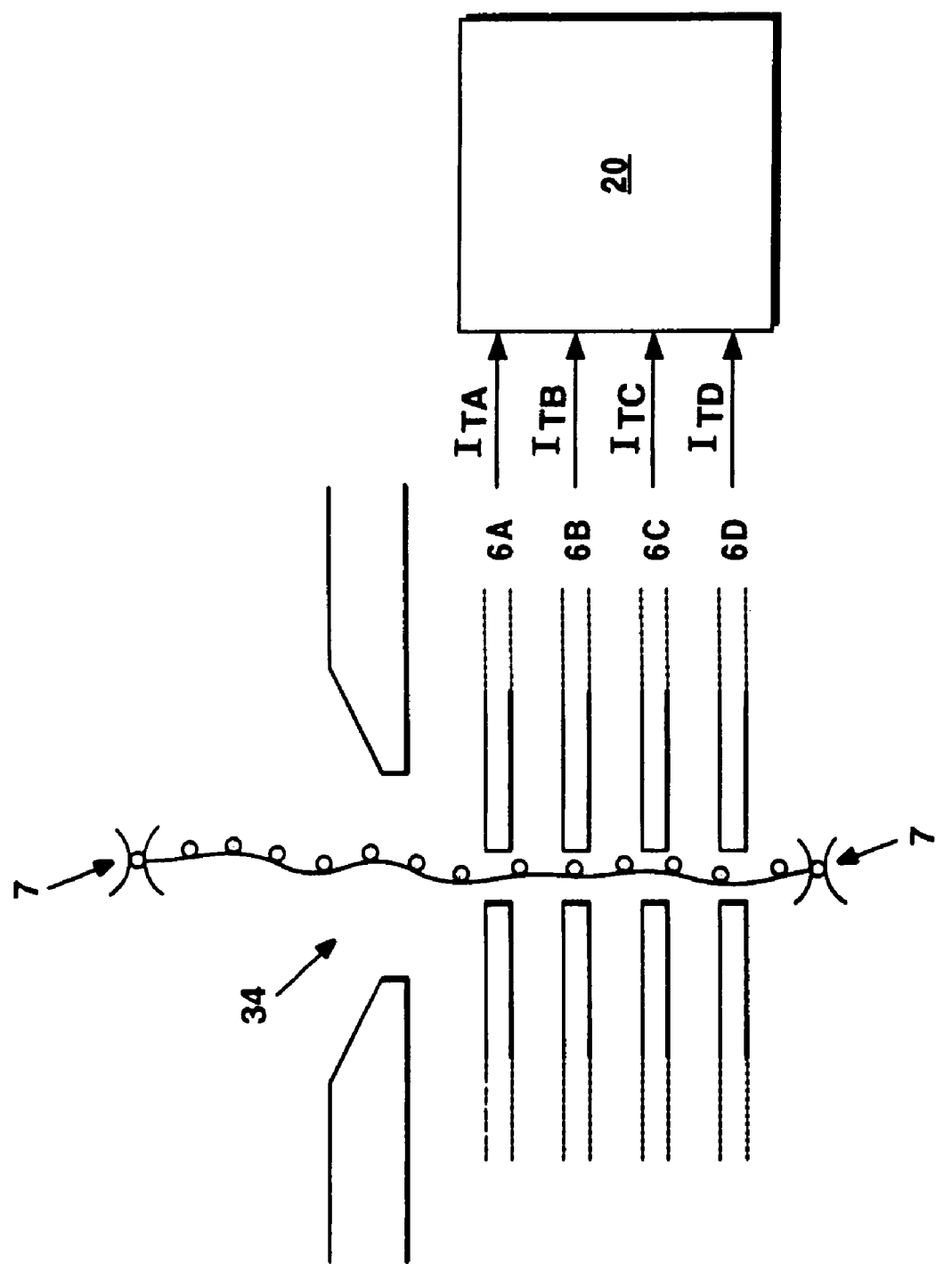

METHOD AND APPARATUS FOR SEQUENCING POLYMERS THROUGH TUNNELING CONDUCTANCE VARIATION DETECTION

BACKGROUND OF THE INVENTION

This invention relates generally to identifying molecules in a polymer chain, and more particularly to sequencing such molecules through tunneling current measurements.

A great deal of research has been performed relating to the functionality of biopolymers, which is determined by the primary sequence of the monomers within the biopolymer. Identifying the sequence of monomers is integral to the understanding of the functionality of the biopolymer. Rapid, reliable, and inexpensive characterization of polymers, particularly nucleic acids, has become increasingly important. Typical current nucleic acid sequencing methods depend either on chemical reactions that yield multiple length DNA fragments cleaved at specific bases, or on enzymatic reactions that yield multiple length DNA fragments terminated at specific bases.

Each of the known methods for sequencing polymers has drawbacks. For instance most of the methods are slow and labor intensive. The gel based DNA sequencing methods require approximately 1 to 3 days to identify the sequence of 300-800 bases in length. Methods such as mass spectroscopy and ELIDA sequencing can only be performed on very short polymers.

Recently, the development of natural or man-made nanopores has enabled rapid determination of the sequence of nucleic acid molecules. In nanopore sequencing, single stranded DNA is passed through a nanopore in a suitable solution and individual nucleotides (or physical changes in the environment of the nucleotide) are physically sensed. For example, a membrane with a nanopore separates two chambers in a solution, between which a low voltage is applied. The ionic current in the solution between the two chambers via the nanopore is used to monitor the presence of the DNA inside the nanopore. When a single stranded DNA is in the nanopore, it partially blocks the nanopore so that the ionic current between the two chambers is decreased. It is proposed to use the change of the ionic current to identify the DNA bases. (See, for example, "Rapid nanopore discrimination between single polynucleotide molecules", Proc. Natl. Acad. Sci. USA. 97:1079-85, 2000; Baldarelli et al., U.S. Pat. No. 6,015,714; and Church et al., U.S. Pat. No. 5,795,782, each incorporated herein by reference.) Since there are typically approximately ten DNA bases in the nanopore at any given time due to the aspect ratio of the nanopore, using ionic current change to identify the individual DNA base is very difficult.

On the other hand, the development in nano-technology makes it feasible to limit the passage of molecules through nanopores. For example, the use of membrane channels to characterize polynucleotides as the molecules pass through the nanopores has been studied. Kasianowicz et al. (Proc. Natl. Acad. Sci. USA. 93:13770-3, 1996, incorporated herein by reference) used an electric field to force single stranded RNA and DNA molecules through a 2.6 nanometer diameter ion channel in a lipid bilayer membrane. The diameter of the channel permitted only a single strand of a nucleic acid polymer to traverse the channel at any given time. As the nucleic acid polymer traversed the channel, the polymer partially blocked the channel, resulting in a transient decrease of ionic current. Since the duration of the decrease in current is directly proportional to the length of the nucleic acid polymer, Kasianowicz et al. (supra) were able to determine experimentally lengths of nucleic acids by measuring changes in the ionic current.

A continuing need exists in the art for the identification and/or sequencing of polymers such as biomolecules that have not previously been identified or characterized.

Described below are improved methods and apparatus for direct sensing or identification of molecules.

SUMMARY OF THE INVENTION

The present invention is directed to the sequential identification of linked molecules in a polymer, such as nucleotide bases of a nucleic acid, by passing the polymer through a nanometer-scale channel formed between a pair of nanoelectrodes. Variation and/or modulation of a bias voltage applied across the nanoelectrodes and subsequent signal processing allows derivation of an electronic characteristic feature or signal that may be compared to known values of the characteristic signal that correspond to desired molecules of interest. The comparison results in the identification of the polymer's molecules in sequence. In the description of the invention provided below, reference is made specifically to preferred embodiments wherein the polymer being sequenced is preferably a nucleic acid, such as a single or double stranded DNA base, however the invention is not meant to be limited to such polymers.

In one aspect, the invention provides apparatus and methods that use the dependence of the tunneling current on the tunneling bias voltage (i.e., variations in tunneling conductance) to identify the molecule under study. The molecular internal structures, e.g., the internal eigenstates, modify the relationship between the tunneling current and the tunneling bias voltage. The modification generates some unique features in the relationship between the tunneling current and the tunneling bias voltage. Therefore they can be used to identify the molecule under study.

The development of nanotechnology makes it feasible to fabricate a pair of nano-scale electrodes such that they have a channel between them on the order of nanometers. Linked molecules of a polymer may then be sequentially passed through the channel and identified using the amplitude of the tunneling current as the criterion while modulating and/or varying the bias voltage across the electrodes. The bias voltage is preferably varied during initial determination of the value(s) of the characteristic feature for a known molecule, in order to identify the bias voltage at which the known molecule is most effectively identified. During identification of the characteristic electrical properties of chemically-known molecules of interest, the bias voltage is centered about the predetermined bias voltage corresponding to a known molecule and then modulated while the molecule(s) of interest are passed through the channel between the nanoelectrodes. The tunneling current and bias voltage are then used to derive the characteristic feature for subsequent comparison to the known value(s) of the characteristic feature in order to identify the molecule(s) of interest in the channel.

A fixed low bias voltage (e.g., 100 mV), for example, may be used for the identification of DNA bases. The bias voltage is centered about a resonance voltage selected to correspond to one or more energy differences between the internal energy levels of a known molecule. Then, as the bias voltage is modulated with a modulation waveform, unknown molecules of interest are sequentially urged through the channel and one or more electrical signals indicative of the molecule of interest are derived by demodulating the tunneling current through the molecule as it passes between the electrodes and the bias voltage. The derived electrical signals are then compared to known values of the signal corresponding to known molecules.

The present invention relies on the relation to the internal energy levels because two dissimilar DNA bases having different orientations with respect to the nano-electrodes as they traverse the channel may appear to have similar tunneling currents (at a fixed bias voltage), complicating identification.

It is preferable to fabricate the electrodes near a nanopore so that the molecules are "funneled" or restricted through the channel a single molecule at a time. The molecules are urged through the electrode channel and/or nanopore by techniques known in the art, such as, for example, application of an electric field, mechanical pressure applied to the solution, or through use of optical tweezers.

In one embodiment of the present invention, the waveform that modulates the bias voltage is a sinusoidal wave having, preferably, all the harmonics of the sine wave suppressed. In another embodiment, the modulation waveform is a square wave. The modulation waveform can be synthetically generated to lack a harmonic to be detected in the derived electrical signal. These techniques and signal choices are intended to enhance a detectable harmonic present in the electrical signal corresponding to the molecule of interest.

The tunneling current is preferably coherently demodulated with a demodulation waveform. Since the methods of demodulation with a demodulation waveform, which can be implemented using analog circuits, digital circuits, or numerical process, is known to the art, no details of the implementation of the demodulator are discussed in order to simplify the discussion here. The demodulation results in certain characteristic features being exhibited. For instance, inelastic electron tunneling in the molecule may exhibit a peak at a resonance voltage in the tunneling current that is demodulated by using the second harmonic of the modulating waveform. Consequently, for the same physical process, the tunneling current, which is demodulated by using the third harmonic of the modulating waveform, may exhibit a dispersion-like curve. Either of these two characteristic signals is useful in comparison to known curves of known molecules. The frequency of the demodulation waveform may be the same as the frequency of the modulation waveform, or be a harmonic or sub-harmonic thereof. Alternatively, the demodulation waveform contains as least one of the following frequency components: the same frequency of the modulation waveform, all the sub-harmonics of the modulation waveform, and all the harmonics of the modulation waveform. The tunneling current may optionally be filtered prior to (e.g., band pass) or after (e.g., low pass) demodulation in order to improve the signal to noise ratio.

In another embodiment, more than one pair of nanoelectrodes may be oriented such that the polymer traverses each channel formed between successive pairs of electrodes. Similar signal processing and/or filtering of each respective modulated tunneling current then allows for simultaneous identification of more than one molecule of interest.

The internal energy level and characteristic electrical features of known molecules are identifiable by conventional techniques such as spectroscopy, however the present invention provides an alternative method. One or more known, identical molecule(s) may be positioned between the nanoelectrodes for a time sufficient to vary the bias voltage across a voltage range encompassing the suspected internal energy level of the molecule and simultaneously modulate the bias voltage with a modulation waveform having a frequency higher than the rate of bias voltage varying. The characteristic electrical signal(s) associated with the known molecule, which can subsequently be used in the comparisons of the method of sequencing described above, are derived by demodulating tunneling currents through the molecule measured as the molecule is between the electrodes. Positioning the known molecule(s) between the nanoelectrodes may be accomplished by holding the molecule(s) in the channel with optical tweezers, or by passing through the nanochannel a polymer comprised of identical molecules through the channel, such that an identical molecule will be present at all times during signal processing.

In another aspect, the present invention provides an apparatus for performing the above studies, comprised of the pair nanoelectrodes to which is connected a signal generator for applying and modulating (and optionally varying) a bias voltage corresponding to one or more energy differences between the internal energy levels of a molecule of interest, a means for urging the polymer through the nanoelectrode channel, and signal processing means for acquiring the tunneling current signal, coherently demodulating the acquired signal and comparing the resultant characteristic electrical signal to known values of the signal associated with known molecules. In optional embodiments, a nanopore or nanochannel may be proximate to the nanoelectrodes so as to restrict the passage of the polymer through the channel to a single molecule at a time. As discussed above, optical tweezers, an electric field generator, or other urging means may be used to force the polymer through the nanoelectrode channel, and filters may be used to improve the signal to noise ratio of the acquired signal.

The signal processor may additionally include a memory for collecting and storing the derived characteristic electrical signals of the molecules of interest, and for retrieval of known values of such signals associated with known molecules for comparison purposes. The present invention offers a higher speed of sequencing (i.e., real-time) and the ability to sequence longer polymers, which is useful in reducing analysis costs such as associated with, for example, nucleotide sequencing.

Other features and advantages of the invention will be apparent from the following description of the preferred embodiments thereof, and from the claims.

BRIEF DESCRIPTION OF THE FIGURES OF THE DRAWING

For a better understanding of the present invention, reference is made to the accompanyings drawing and detailed description, wherein:

FIG. 3 is a schematic view of portion of an apparatus for simultaneously identifying multiple molecules in a polymer in accordance with the present invention.

DETAILED DESCRIPTION OF PREFERRED EMBODIMENTS OF THE INVENTION

Figure 1:
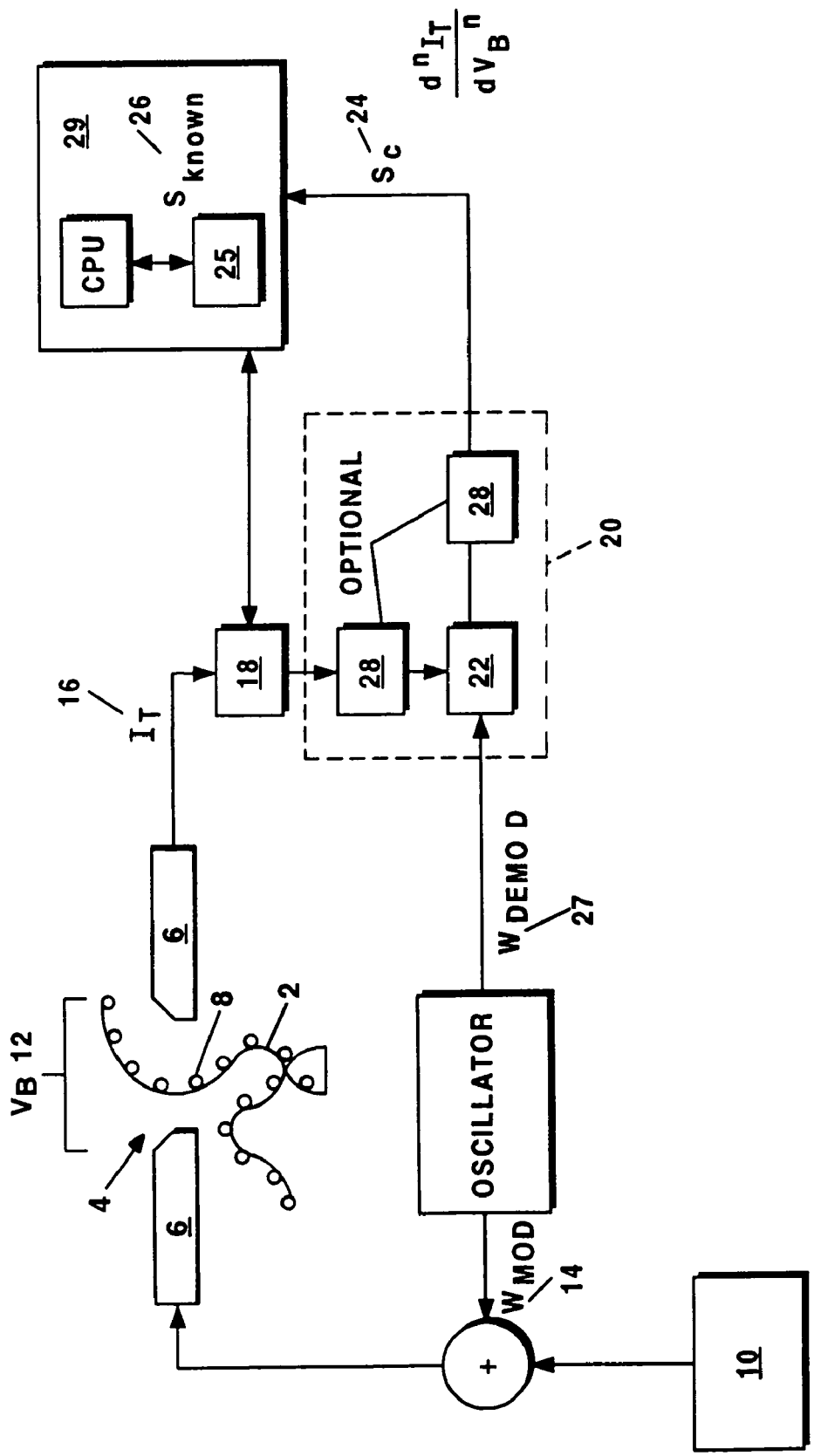
FIG. 1 is a schematic view of components comprising an apparatus for sequencing a polymer in accordance with the present invention.

The present invention provides systems and methods for sequencing polymers. With reference to FIG. 1 (which is not drawn to scale), a preferred embodiment of the present invention involves urging the polymer 2 in solution across a channel 4 between a pair of nano-electrodes 6 one molecule 8 at the time, and using a conventional signal generator 10 to center a bias voltage $V_B$ 12 across the electrodes 6 that corresponds to the energy difference between any two of the internal energy levels of the molecule 8 of interest. A modulation waveform $W_{MOD}$ 14 is then applied to the bias voltage $V_B$ 12. A tunneling current $I_T$ 16 traversing the channel 4 through the molecule 8 is acquired by a sensor 18 (e.g., a current sensor) and relayed to signal processing equipment 20, which can include a lock-in amplifier and/or phase sensitivity detector. The acquired tunneling current $I_T$ 16 is then demodulated by demodulator 22 in order to derive a characteristic signal $S_C$ 24

$$\left(\frac{d^n I_T}{dV_B^n}\right)$$

that can then be compared to a predetermined signal $S_{KNOWN}$ 26 associated with a known molecule for a determination whether the molecule 8 traversing the channel 4 is identical to the known molecule. The acquired tunneling current $I_T$ 16 may optionally be passed to a either a band pass or low pass filter 28, respectively, before or after demodulation. Conventional techniques can be employed to accomplish the comparison of the derived characteristic signal $S_C$ 24 to the predetermined signal $S_{KNOWN}$ 26, such as through linear and/or non-linear curve-fitting and/or variation analyses (e.g., Allan Deviation.)

Figure 2:
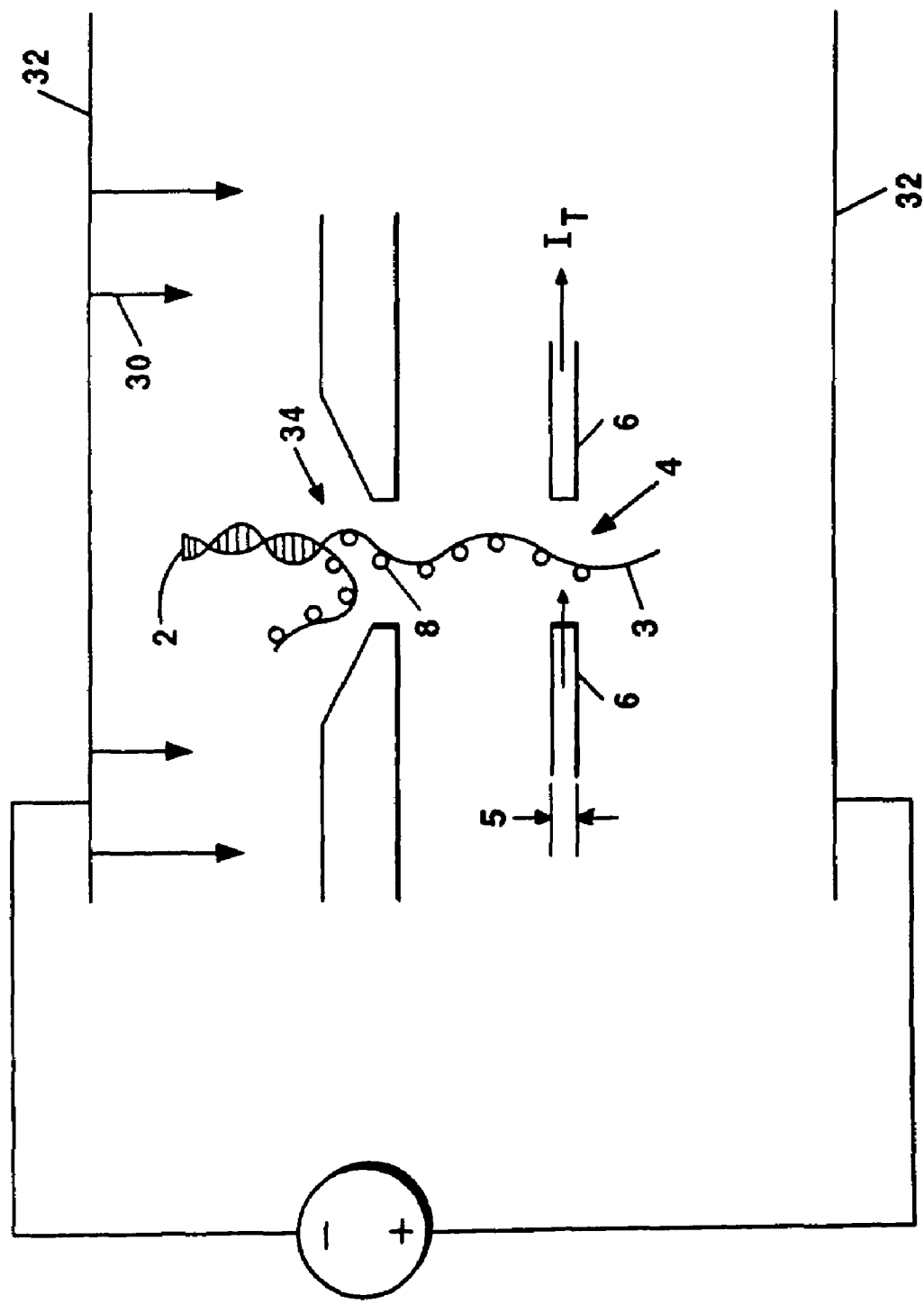
FIG. 2 is a schematic view of nanoelectrodes with a funneling means and electrophoretic field generator in accordance with the present invention.

With reference to FIG. 2, the polymer 2 may be any type of polymer known in the art, but preferably comprises a nucleic acid or a protein. DNA is a polymer of deoxyribonucleotides, which are comprised of deoxyribose, one or more phosphate groups, and a derivative of adenine (A), guanine (G), thymine (T) and cytosine (C). The genetic information of a DNA strand 3 can be determined by sequencing the four distinct bases (A, G, C, and T) in the strand 3. RNA may also be sequenced, recognizing that RNA strands include uracil (U) molecules instead of thymine among the four bases. The DNA strand may be single-stranded or double-stranded, and known techniques may be applied to reduce an initially double-stranded sample to a single stranded and/or to eliminate secondary DNA structures. For convenience, any conventional method may be employed to dissociate a double-stranded DNA strand into single-stranded, such as by disrupting the hydrogen bonds between paired bases with heat or ionizing acids or alkalis.

The solution in which the polymer 2 is distributed may be any fluid that permits adequate polymer mobility across the nano-electrode channel 4 for sequencing. Such solutions generally contain ions as the current conducting agents, e.g., barium, calcium, cesium, chloride, phosphate potassium, sodium, or sulfate and are preferably, but not necessarily, water-based to simulate in vivo conditions. The polymer 2 can be urged into or through the channel 4 by establishing and adjusting (to zero and/or reversing the polarity thereof) an electrophoresis electric field 30 that is non-parallel to the nano-electrodes 6 by means of a pair of electrodes 32 disposed one each on each side of the nanoelectrodes 6. (see Proc. Natl. Acad. Sci. USA Vol. 93, pp. 13770-13773, November 1996, incorporated herein by reference) Other means for urging the polymer through the channel 4 may be employed, such as application of mechanical pressure to the solution on only one side of the nano-electrodes 6, or through use of optical tweezers (shown in FIG. 3 as element 7.) The polymers 2 can also be induced to traverse the channel by physically linking a catalyst to ends of the polymeric chain and dragging the polymer by displacing the catalyst.

The nanoelectrodes 6 should be insulated to prevent current losses and can be constructed using existing nanoscale manufacturing technology to various sizes and shapes of materials conductive but inert to the solution (e.g., gold.) (See "Rapid nanopore discrimination between single polynucleotide molecules", A. Meller, et al., Proc. Natl. Acad. Sci. USA Vol. 97, pp. 1079 (2000).) Monolayers and sub-monolayers of atoms can be precisely deposited or depleted to exacting specifications. Furthermore, electrolytic metal-dissolving reactions may be used to open and control nanopores or nanochannels in metals, and to control channel sizes between nanoelectrode tips. Known nanolithography methods include, but are not limited to chemical vapor deposition, electrochemical deposition, chemical deposition, electroplating, thermal diffusion and evaporation, physical vapor deposition, sol-gel deposition, focused electron beam, focused ion beam, molecular beam epitaxy, dip-pen nanolithography, reactive-ion beam etching, chemically assisted ion beam etching, microwave assisted plasma etching, electro-oxidation, scanning probe methods, chemical etching, nanoprinting and laser ablation.

The characteristics of the molecule 8 traversing the channel 4 can be identified by the amplitude or duration of tunneling conductance changes across the nanoelectrodes 6. Each type of molecule will exhibit a characteristic feature enabling identification of the molecule. The volume, shape, or charges on each monomer will affect conductance in a characteristic way. Additionally, the size of the entire polymer 2 can be determined by observing the duration of conductance changes. The tunneling conductance changes are efficiently determined by modulating the bias voltage $V_B$ 12 and then demodulating the tunneling current $I_T$ 16 acquired from the nanoelectrodes 6, one of the nanoelectrodes serving as an anode and the other as a cathode electrode. The width of the channel 4 between the nanoelectrodes 6 is on the order of nanometers and the length 5 on the order or smaller than the space between the base molecules on the strand 3. The exact shape of the nanoelectrodes is not important, provided that the channel length and thickness are relatively small. It is expected that the width of the channel 4 between the nanoelectrodes cannot be made perfectly uniform, however, because the measurable tunneling current rises approximately as an exponential function of the width, the signals attributable to the tunneling current across the molecule as it passes the point of narrowest width will dominate the measurements. This actually has a beneficial effect of limiting tunneling current effects of additional, undesired molecules that may be present in the channel with the particular molecule of interest (e.g., because the length of the channel between the nanoelectrodes undesirably allows more than one molecule between the nanoelectrodes.)

The dimensions of the channel 4 may serve to constrain the molecules so that they are restricted to passage between the nanoelectrodes on a molecule-by-molecule basis, but it is preferable to alternatively first "funnel" the polymer 2 through a solid-state nanochannel or nanopore, or natural nanopore (such as α-hemolysin) 34 in order to reorder or reorient the molecules. The nanopore should be formed of a nonconductive material such as, for example, silicon nitride, which is similarly inert to the solution and can be created using one of the techniques described above.

Referring again to FIG. 1, signal generator 10 provides the bias voltage $V_B$ 12 and modulation waveform $W_{MOD}$ 14 supplied to the nanoelectrodes 6. The sensor 18 is used to interrogate the nanoelectrodes to measure time-dependent tunneling current $I_T$ 16 variations. The acquired tunneling current $I_T$ 16 signals can be stored in an optional data storage device 25 for later analysis, or processed immediately using a high throughput, real-time method. In either approach, the acquired tunneling current $I_T$ 16 signals are passed to demodulator 22 where a demodulation waveform $W_{DEMOD}$ 27 is applied. The resultant characteristic "feature" or signal $S_C$ 24 can then be compared to a predetermined signal or signals $S_{KNOWN}$ 26 characteristic of or associated with a known molecule to determine the relationship (e.g., identity) between the molecule of interest 8 and the known molecule.

According to quantum mechanics, the tunneling current, $I_T$ 16 is a linear function of the bias voltage, $V_B$ 12, so that the tunneling conductance, defined as $dI_T/dV_B$, is a constant for a given orientation of a molecule 8 with respect to the nanoelectrodes 6. This approximation is accurate only for low bias voltages since it does not include effects attributable to the internal states of the molecule 8. Taking into account the molecular internal states, the tunneling conductance is modified when the energy of the tunneling electron is in the vicinity of $\Delta\epsilon_{ij} \equiv \epsilon_i - \epsilon_j$, where $\epsilon_i$ and $\epsilon_j$ are the energies of the state |i> and the state |j> of the molecule, respectively. A corresponding "resonance voltage" can be determined from the variation of the tunneling conductance, and can be used to identify the molecule 8 under study. The values of these "resonance voltages" are expected to be less sensitive to the orientation of the (e.g., DNA base) molecule since they are determined by the internal states of the molecule 8. The details of the influence of the different quantum states on the tunneling conductance depend on the physical processes involved. For instance, in some molecules the inelastic electron tunneling is the dominant process, which modifies the tunneling conductance, at least within a small range of the tunneling electron energy.

The energy of a molecular state is determined by its electronic, vibrational, and rotational quantum numbers. The energies associated with electronic, vibrational, and rotational states in a molecule are on the orders of eV, 100 meV, and 100 µeV, respectively. Thus the vibrational states in the ground electronic state would be the most suitable states for the purpose of identifying the molecules of interest using the method discussed.

In order to initially identify the characteristic signal or signals associated with a particular molecule, either a single known molecule needs to be positioned in the channel 4 between the nanoelectrodes (e.g., with optical tweezers), or a polymer strand comprised of repeating molecules needs to be generated and passed through the channel. Any techniques known in the art for enzymatically generating, preferably single-stranded, nucleic acids with repeating sequences with reduced or eliminated secondary structures may be employed. Once the molecule 8 of interest is in the channel 4 between the nanoelectrodes 6, the bias voltage $V_B$ 12 can be swept (linearly or non-linearly) over the range of interest, i.e., a voltage range that encompasses the expected resonance voltage(s) of the molecule 8. The tunneling bias voltage $V_B$ 12 and the corresponding tunneling current $I_T$ 16 acquired by sensor 18 can optionally be stored in data storage device 25 for later processing to reveal these "resonance voltages."

Characteristics attributable to inelastic electron tunneling are observable and useful in deriving identification information. In this process, the second derivative of the tunneling current $I_T$ 16 with respect to the bias voltage, $d^2 I_T/dV_B^2$, shows a detectable peak at the "resonance voltage." (see "Single-Molecule Vibrational Spectroscopy and Microscopy", B. Stipe, et al., Science, Vol. 280, pp. 1732-1735, 12 Jun. 1998, incorporate herein by reference.) If a different physical process is occurring, the characteristics of the tunneling current at the "resonance voltage" might be different. Then $d^n I_T/dV_B^n$ (with a different value of n) will show some characteristic feature, e.g., a peak, at the "resonance voltage." The bandwidth of this method is relatively large since the bias voltage $V_B$ 12 is to be swept over the range of interest during the dwell time of a single molecule 8 in the channel 4 between the nanoelectrodes 6.

Alternatively, the bias voltage $V_B$ 12 can be modulated (dithered) with modulation waveform $W_{MOD}$ 14 at modulation frequency $f_m$. The signal $d^n I_T/dV_B^n$ can be obtained by demodulating the tunneling current $I_T$ 16 with the nth harmonic of the modulation frequency. The characteristic feature sought will show up when the bias voltage $V_B$ 12 scans across the "resonance voltage." Modulation waveform $W_{MOD}$ 14 is preferably generated such that it is lacking a harmonic signal that is expected to be found in the characteristic signal. Appropriate waveforms can include, for example, square waves or sine waves in which all harmonics of the sine wave have been suppressed. The modulation waveform may also be synthetically generated such that it enhances the harmonic in the characteristic signal in some manner. The acquired tunneling current signal is coherently demodulated with demodulation waveform $W_{DEMOD}$ 27 to derive the characteristic signal(s). The demodulation waveform may have the same frequency $f_m$ as modulation waveform $W_{MOD}$ 14, or a harmonic or sub-harmonic thereof. Alternatively, the demodulation waveform may contain as least one of the following frequency components: the fundamental frequency of the modulation waveform, all the sub-harmonics of the modulation waveform, and all the harmonics of the modulation waveform. For certain molecules, the inelastic electron tunneling will exhibit a peak in the tunneling current demodulated by using the second harmonic of the modulating waveform. Consequently, it will exhibit a dispersion-like curve in the tunneling current demodulated by using the third harmonic of the modulating waveform.

After the characteristic signal $S_{KNOWN}$ of the tunneling conductance has been initially determined for a particular molecule, either through the method described above or vibrational spectroscopy, one can interrogate unknown molecules of interest to determine if they exhibit the known characteristic signal(s), and thereby identify the molecules of interest. This is accomplished in one method by centering the bias voltage (with modulation) at the unique "resonance voltage" for a known molecule. When a molecule of interest of the known type passes through the channel 4 between the nanoelectrodes 6, the signal derived from the demodulated tunneling current will exhibit the characteristic feature in the time domain. The characteristic feature plotted against time (fixed bias voltage) may look different in comparison with the characteristic feature of the same molecule plotted against the scanning bias voltage. In this detection mode, the detection bandwidth is determined by the dwell time of the molecule in the channel so that the signal-to-noise ratio will be greatly improved.

In one embodiment, the comparison function of known and unknown characteristic signals is implemented directly in discrete or integrated hardware components. In another embodiment, detected tunneling currents $I_T$ are optionally stored in data storage device 25 for analysis whenever desired to determine structural information about the polymer. The computer 29 suitable for use in the present invention includes an output device and input device for interfacing with a user and the data storage device, and a processor with executable memory space for conducting analyses connected to the data storage device. The input and output devices are also connected to the processor and memory system. Computer programs to perform the data analysis of the detected signals described above are readily available.

With reference to FIG. 3, in another embodiment of the present invention, multiple pairs of nanoelectrodes 6a-6d independently identify molecules passing through their respective channels. They may share signal processing equipment 20. Each respective bias voltage applied to each pair of nanoelectrodes 6a-6d is centered about a resonance voltage associated with a unique, known molecule and is modulated at a unique modulation frequency. Care should be taken to assure that bias voltages between successive pairs of nano-electrodes do not interfere with one another, such as through insulation or shielding. The tunneling currents $I_{TA}$ through $I_{TD}$ collected from each corresponding pair of nano-electrodes 6a-6d are demodulated simultaneously by demodulators as described above at a respective desired harmonic of the particular modulation frequency. As also described above, optional filtering can be used before and/or after demodulation to improve the signal to noise ratio. For a given molecule, the corresponding demodulated signal will show the characteristic feature sought when it passes an appropriate detector tuned to that molecule. This apparatus and method allows several different molecules to be identified and a polymer to be sequenced in a very rapid manner.

Successive pairs of nano-electrodes are not required to be aligned as depicted in FIG. 3; some angle or offset is allowable. Additionally, it is not necessary for each pair of nano-electrodes to identify different molecules of interest. For example, each pair may employ different resonance voltages to search for different characteristic signals of the same unknown molecule. It may be the case that more than one resonance voltage employed on different pairs of nano-electrodes to identify a particular molecule are necessary or desirable to increase detection/identification reliability. The derived signals and the timing of molecule passage through the respective channels can be correlated in cases where multiple pairs of nano-electrodes are employed.

There is no limit known to the inventor on the length of polymer that can be sequenced employing the present invention, however, the present invention provides optimal results when the polymer being sequenced has a linear, curved or straight backbone, as difficulties may be encountered in the optional step of straightening (i.e., funneling) the polymer if the polymer has too irregular a shape. The desire for an optimal throughput will also pragmatically limit how slowly the polymer will be sequenced—slower speeds will produce better signal to noise ratios, but at the lowest speed limits Brownian motion will generate ambiguities. Thus, the erging method should be selected to eliminate Brownian motion effects and increase throughput.

Although the invention has been described with respect to various embodiments, it should be realized this invention is also capable of a wide variety of further and other embodiments within the spirit of the invention.

What is claimed is:

1. A method of sequencing molecules of a polymer, comprising the steps of:
    centering a fixed bias voltage across a pair of nano-electrodes separated by a channel therebetween, the bias voltage corresponding to an energy difference between any two internal energy levels of a molecule of interest;
    modulating the bias voltage with a modulation waveform;
    sequentially urging the molecules of a polymer comprised of linked molecules including at least one of the molecules of interest through the channel;
    deriving an electrical signal indicative of the molecule of interest from tunneling current through the molecule of interest measured while the molecule of interest is between the nano-electrodes as the polymer passes through the channel; and
    identifying the molecule of interest by comparing the derived electrical signal to known values of the signal for the molecule of interest.

2. The method of claim 1, wherein the sequential urging step further comprises the step of funneling the polymer into the channel to restrict the passage of the polymer through the channel to a single molecule at a time.

3. The method of claim 2, wherein the funneling step further comprises forcing the polymer through a nanopore or nanochannel.

4. The method of claim 1, wherein the polymer is a nucleic acid.

5. The method of claim 4, wherein the polymer is double-stranded DNA and the molecule of interest comprises a DNA base or a pair of DNA bases.

6. The method of claim 4, wherein the polymer is single-stranded DNA and the molecule of interest comprises a DNA base.

7. The method of claim 1, wherein the sequential urging step further comprises one of driving the polymer with an electric field, applying mechanical pressure to a solution in which the polymer is suspended, or directly manipulating the polymer with one or more pairs of optical tweezers.

8. The method of claim 1, wherein the modulation waveform is selected from the group consisting of a sine wave, a sine wave wherein all harmonics of the sine wave are suppressed, a square wave, a synthetically generated waveform lacking an harmonic to be detected in the derived electrical signal, and a synthetically generated waveform that enhances at least one of the desired harmonics present in the derived electrical signal corresponding to the molecule of interest.

9. The method of claim 1, wherein the step of deriving the characteristic electrical signal further comprises demodulating the tunneling current coherently with a demodulation waveform.

10. The method of claim 9, wherein inelastic electron tunneling in the molecule exhibits a peak in the tunneling current demodulated with the second harmonic of the modulation waveform.

11. The method of claim 9, wherein inelastic electron tunneling in the molecule exhibits a dispersion-like curve in the tunneling current demodulated with the third harmonic of the modulation waveform.

12. The method of claim 9, wherein the demodulation waveform contains at least one of the following frequency components: the same frequency of the modulation waveform, all the sub-harmonics of the modulation waveform, and all the harmonics of the modulation waveform.

13. The method of claim 9, further comprising the step of filtering of the tunneling current to improve the signal to noise ratio.

14. The method of claim 9, wherein the deriving step further comprises extracting the signal from the demodulated tunneling current by filtering and/or post-processing.

15. The method of claim 1, wherein the electrical signal comprises a resonance voltage determined from variations in tunneling conductance resolved from the tunneling current.

16. The method of claim 15, wherein the bias voltage corresponds to the resonance voltage for the molecule of interest.

17. The method of claim 1, further comprising:
centering at least one additional bias voltage across at least one additional pair of nano-electrodes separated by a channel so as to form at least one additional channel therebetween, the at least one additional bias voltage corresponding to the energy difference between any two internal energy levels of at least one additional molecule of interest;
modulating the at least one additional bias voltage with at least one additional modulation waveform;
urging the polymer through the at least one additional channel;
deriving at least one additional electrical signal indicative of the at least one additional molecule of interest from tunneling current between each respective pair of electrodes measured while a molecule portion of the polymer passes through the respective channel; and
identifying at least one additional molecule of interest by comparing the respective derived electrical signals to known values of the signals for the molecules of interest by a single passage of the polymer through the channels.

18. The method of claim 1, further comprising:
centering at least one additional bias voltage across at least one additional pair of nano-electrodes separated by a channel so as to form at least one additional channel therebetween, the at least one additional bias voltage corresponding to the energy difference between any two internal energy levels of the molecule of interest;
modulating the at least one additional bias voltage with at least one additional modulation waveform;
urging the polymer through the at least one additional channel;
deriving at least one additional electrical signal indicative of the molecule of interest from tunneling current between each respective pair of electrodes measured while a molecule portion of the polymer passes through the respective channel; and
further identifying the molecule of interest by comparing the respective derived electrical signals to known values of the signals for the molecules of interest by a single passage of the polymer through the channels.

19. A system for sequencing molecules of a polymer, comprising:
a pair of nano-electrodes arranged to sequentially receive linked molecules of a polymer in solution in a channel formed therebetween;
a signal generator electrically connected to the nano-electrodes an configured to center a fixed bias voltage across the nano-electrodes corresponding to the energy difference between any two internal energy levels of a molecule of interest and to modulate the bias voltage with a modulation waveform;
means for urging the polymer through the channel;
means for measuring tunneling current between the nano-electrodes while a molecule portion of the polymer passes through the channel; and
signal processor for deriving an electrical signal indicative of the molecule of interest from the tunneling current and identifying the molecule of interest by comparing the derived electrical signal to known values of the electrical signal for the molecule of interest.

20. The system of claim 19, further comprising means for restricting the passage of the polymer between the channel to a single molecule at a time.

21. The system of claim 20, wherein the restricting means comprises a nanopore or nanochannel.

22. The system of claim 19, wherein the urging means is selected from the group consisting of electrodes establishing an electric field applied to the solution, mechanical means creating a pressure gradient across the channel between the nano-electrodes, and one or more pairs of optical tweezers.

23. The system of claim 19, wherein the modulation waveform lacks an harmonic to be detected in the derived electrical signal.

24. The system of claim 19, wherein the modulation waveform enhances at least one of the desired harmonics present in the electrical signal corresponding to the molecule of interest.

25. The system of claim 19, wherein the signal processor demodulates the tunneling current coherently with a demodulation waveform.

26. The system of claim 25, wherein the demodulation waveform contains as least one of the following frequency components: the same frequency of the modulation waveform, all the sub-harmonics of the modulation waveform, and all the harmonics of the modulation waveform.

27. The system of claim 25, further comprising one or more tunneling current filters for improving the signal to noise ratio prior to demodulation.

28. The system of claim 19, wherein the electrical signal comprises a resonance voltage determined from variations in tunneling conductance resolved from the tunneling current.

29. The system of claim 28, wherein the bias voltage corresponds to the resonance voltage for the molecule of interest.

30. The system of claim 19, wherein the signal processor further comprises a data storage device for collecting and storing the derived electrical signals.

31. The system of claim 30, wherein the signal processor is further arranged to access records of known electrical signals associated with molecules of interest stored in the data storage device for comparison to the derived electrical signals.

* * * * *